United States Patent [19]

Snyder et al.

[11] 4,331,262

[45] May 25, 1982

[54] CALIBRATABLE AUTOMATIC FLUID DISPENSER

[75] Inventors: Philip Snyder, Lawrenceville; David Freedman, Highland Park, both of N.J.

[73] Assignee: New Brunswick Scientific Co., Inc., Edison, N.J.

[21] Appl. No.: 72,859

[22] Filed: Sep. 5, 1979

Related U.S. Application Data

[63] Continuation-in-part of Ser. No. 894,317, Apr. 7, 1978, Pat. No. 4,170,861.

[51] Int. Cl.³ .............................................. B67D 5/30
[52] U.S. Cl. .......................................... 222/37; 73/3; 73/168; 141/196; 222/14; 222/63; 222/70; 364/571
[58] Field of Search ................................. 222/14–22, 222/23, 25, 26–28, 36, 37, 63, 70; 141/192, 196; 364/478, 479, 571, 509, 510; 324/166; 73/3, 168

[56] References Cited

U.S. PATENT DOCUMENTS

| | | | |
|---|---|---|---|
| 2,759,633 | 8/1956 | Ross | 222/16 |
| 2,826,067 | 3/1958 | Bravnlich | 73/168 |
| 2,966,175 | 12/1960 | Hyde | 222/37 X |
| 3,011,684 | 12/1961 | Corneil | 222/70 X |
| 3,756,292 | 9/1973 | Croslin et al. | 222/37 X |
| 3,768,510 | 10/1973 | Reves | 73/3 UX |
| 3,872,723 | 3/1975 | Busch | 73/168 |
| 3,887,110 | 6/1975 | Porter | 222/63 X |
| 3,935,971 | 2/1976 | Papoff et al. | 222/26 X |
| 4,073,304 | 2/1978 | Lerner et al. | 73/168 X |
| 4,171,638 | 10/1979 | Coman et al. | 73/168 X |

FOREIGN PATENT DOCUMENTS

| | | | |
|---|---|---|---|
| 2532033 | 2/1977 | Fed. Rep. of Germany | 324/166 |
| 2272899 | 12/1975 | France | 222/14 |
| 943330 | 12/1963 | United Kingdom | 222/14 |

Primary Examiner—Robert J. Spar
Assistant Examiner—Edward M. Wacyra
Attorney, Agent, or Firm—Blum, Kaplan, Friedman, Silberman and Beran

[57] ABSTRACT

A fluid dispenser pumps fluid in increments. The dispenser includes a computer which, on command, determines the volume of fluid dispensed per increment, the determined value constituting a calibration value which is stored in the memory of the computer. A controller which may include the computer as a component provides for dispensing a selected number of doses, each of a selected volume. The controller can also specify a time interval between the delivery of successive doses. The dispenser is particularly useful in combination with apparatus for charging petri dishes with agar.

14 Claims, 7 Drawing Figures

CALIBRATABLE AUTOMATIC FLUID DISPENSER

CROSS-REFERENCE TO RELATED APPLICATIONS

The present application is a continuation-in-part of our U.S. Pat. No. 4,170,861 issued Oct. 16, 1979 and having the title Method and Apparatus for Filling Petri Dishes.

BACKGROUND OF THE INVENTION

The problem of dispensing fluid doses of a selected volume is met in many fields, particularly in the pharmaceutical field. Apparatus for charging a large number of petri dishes automatically with agar is disclosed in the above-identified application. While a number of devices are already available, the accuracy and precision of such devices when compared with the cost of same are not as great as could be desired. One difficulty is that the delivery system may not have been properly calibrated initially. Another difficulty arises from the fact that the volume of liquid delivered per stroke or per revolution may change with time. This is particularly the case where pumps which are based on compression of rubber tubing are concerned. The internal diameter of the rubber tubing varies from lot to lot, and the flexibility of the rubber decreases with age. Accordingly, it would be desirable that a device be provided which makes it possible to calibrate the pump easily and as often as desired. Further, in view of the fact that fluid dispensers are frequently called upon to dispense repetitively a large number of doses, it would be desirable that the device be capable of dispensing a selected number of doses, each of a selected size, automatically. In addition, the device should be capable of introducing a hiatus between successive doses to provide for moving fresh containers into place at the delivery point. The present invention is designed to provide these capabilities.

SUMMARY OF THE INVENTION

An automatic fluid dispenser in accordance with the present invention includes pump means which transfer fluid through a conduit in increments. Such increments could correspond to strokes of a diaphragm pump, individual rollers compressing a flexible tube and moving along the tube to push a quantity of liquid therethrough, and gear pumps in which the increment corresponds to the volume between successive teeth on a gear. The pump means is driven by a motor which, preferably, also drives counter means which count the number of increments delivered in dispensing a selected volume of fluid. The selected volume of fluid, that is, the volume of fluid delivered in the selected number of increments, may be determined either automatically or by an observer in a calibration procedure.

Computer means, on command, compare the volume of fluid delivered with the number of increments required to deliver said volume and determine therefrom a "calibrated value" which is stored retrievably in the memory of the computer means. Calibration means are provided for issuing a command to the computer means for storing said calibrated value, and controller means are provided for causing the fluid dispenser to deliver a selected volume of fluid, either as a single dose or repetitively. The controller means are arranged and constructed for dispensing said doses at selected intervals to provide time for moving a receiver into place at the point of dispensing said fluid. By reduction of the interval between successive doses to zero, the dispenser can be arranged to dispense liquid continuously. The controller is also arranged and constructed for shutting off the dispenser after the dispensing of a selected number of doses, each of a selected volume. If desired, the controller can be set to emit a signal to indicate that the selected number of doses has been delivered.

Counting of the increments can be effected by optical, mechanical, magnetic or electric means, using appropriate sensors.

The dispenser is particularly effective when used in combination with apparatus for charging, repetitively, a large number of petri dishes with agar. Where the dispenser is to be used for this purpose, it may constitute a component of the petri-dish filling apparatus.

Accordingly, an object of the present invention is a fluid dispenser for dispensing a selected number of doses, each of a given volume, said fluid dispenser being readily calibratable.

Another object of the present invention is a fluid dispenser which dispenses a selected volume of fluid in increments.

A further object of the present invention is a fluid dispenser which dispenses fluid in increments, said dispenser being readily calibratable by determining the number of increments necessary to dispense a selected volume of fluid, and the calibration value determined in this way being storable in computer means constituting a component of said fluid dispenser.

An important object of the present invention is a fluid dispenser of simple construction, the simplicity being achieved in part by driving pump means and counter means by the same motor.

A significant object of the present invention is a fluid dispenser which can readily be calibrated and which can be used to advantage with apparatus for charging petri dishes with agar.

Still other objects and advantages of the invention will in part be obvious and will in part be apparent from the specification.

The machine accordingly comprises the features of construction, combinations of elements, and arrangement of parts which will be exemplified in the constructions hereinafter set forth, and the scope of the invention will be indicated in the claims.

BRIEF DESCRIPTION OF THE DRAWINGS

For a fuller understanding of the invention, reference is had to the following description, taken in connection with the accompanying drawings, in which.

DESCRIPTION OF THE PREFERRED EMBODIMENTS

Figure 1:
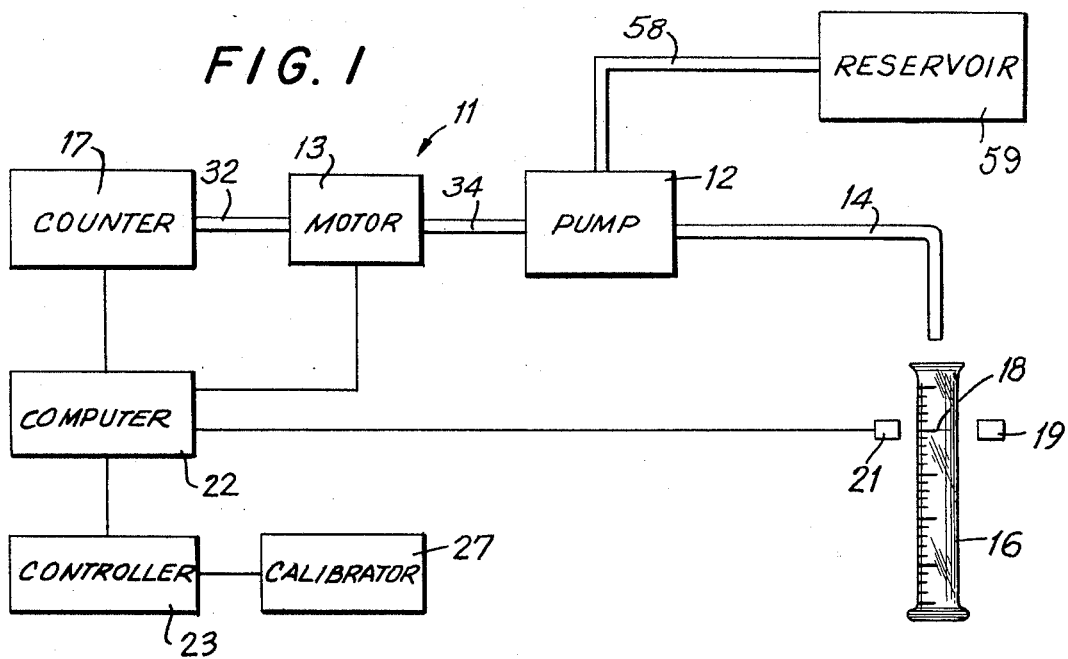
FIG. 1 shows schematically the components of a fluid dispenser in accordance with the present invention.
Figure 6:
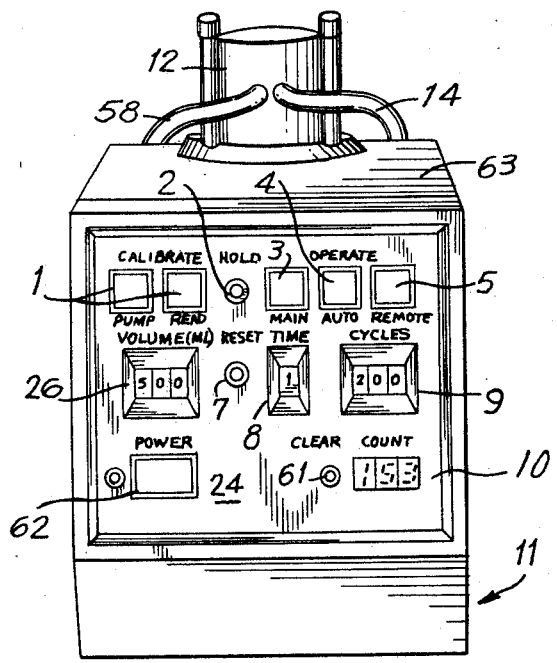
FIG. 6 is a perspective view of an apparatus in accordance with the present invention showing control details.

An embodiment of the present invention is shown in perspective in FIG. 6 and schematically in FIG. 1. Considering FIG. 1 first, the fluid dispenser indicated generally by the reference numeral 11 includes pump means 12 drive by motor 13. Pump means 12 transfers fluid through a conduit 14 to a single receiver or a series of receivers (not shown) in normal operation. Receiver 16 is used for calibration of the device.

Pump means 12 is any of the types which deliver or transfer fluid in small increments, examples being those in which rollers compress a flexible tube and move along the tube pushing the liquid therethrough, the volume between the regions at which two successive rollers compress the tubing constituting the increment. Alternatively, the pump may be of the diaphragm type in which the increment corresponds to one cycle of the diaphragm or may be of the gear-pump type in which the increment corresponds to the fluid between successive teeth on a gear or lobes on a cam. The roller pump is preferred because of the ease with which the tubing may be changed either to change the size of the increment or to replace a tube which has lost flexibility as the result of aging.

Counter means 17 are provided for counting the number of increments transferred or dispensed during a delivery operation. Preferably, counter means 17 and pump means 12 are driven by the same motor, thereby ensuring complete accuracy in the number of revolutions of the pump or cycles of the pump and, consequently, in the number of increments of fluid dispensed, since the number of increments per revolution or cycle of the pump is known from the construction thereof.

To calibrate the dispenser, the pump is operated until the dispensed fluid in receiver 16 reaches a selected level 18. The level may be detected by means of a suitable light source 19 in combination with an optical sensor 21. Where the fluid is transparent, an opaque float may be placed in the receiver to intercept the light beam from light source 19. Alternatively, the pump may be stopped by an operator when the volume of fluid dispensed into receiver 16 reaches the desired level 18.

Computer means 22 is connected with counter 17, which transmits to said computer means the number of increments which have been dispensed. Also, the volume dispensed is transmitted to computer means 22 from optical sensor 21 either over the lines shown or by manual input from the operator. Computer means 22 on command from controller means 23 then divides the dispensed volume by the number of increments required to dispense said dispensed volume and arrives at a "calibrated value," which is the volume of liquid dispensed per increment. The computer then stores this value in its memory retrievably and replaceably. The controller means 23 has a panel 24 which includes a dial 26 which can be set to any digital value from zero up to its full range, dial 26, as shown in FIG. 6, having a range of zero to 99.9 ml.

As is evident, there are at least two different ways in which the calibration can be carried out readily, the first being to dispense a selected volume and to count the number of increments and the second being to dispense a selected number of increments and to measure the delivered volume. In each case, the counting may be done automatically by the calibration means in combination with the computer and controller. Furthermore, in each case, the volume delivered may be measured either automatically by means of an appropriate sensor or determined by an observer, who then transfers the volume data into the memory of the computer. In the embodiment shown in FIG. 6, calibration mode switches 1,1 allow the pump to operate for a fixed number of revolutions or cycles and thereby to dispense a fixed number of increments. Also, the volume of fluid dispensed into the receiver 16 as determined by an observer may be put into the computer. The calibration mode switches then command the computer to determine the volume per increment and to store this figure as a calibrated value in the memory of the computer means.

Figure 2:
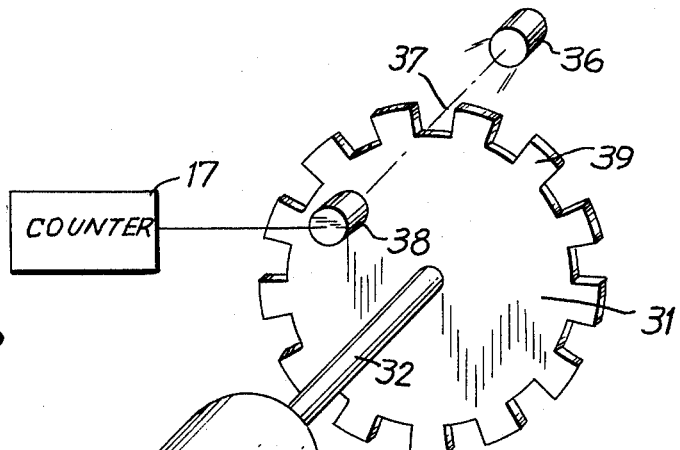
FIGS. 2, 3 and 4 are perspective views of counter means for counting increments of fluid by means, respectively, of an optical sensor, a magnetic sensor and an electrical sensor.

Counting of the increments may be effected as shown in FIGS. 2–5. In FIG. 2, a toothed disk 31 is mounted fixedly to shaft 32 driven by motor 33. Motor 33, preferably, is also connected by means of shaft 34 to pump means 12. As a result of driving disk 31 and pump means 12 by means of the same motor 33, synchronous rotation of pump 12 with disk 31 is ensured. A light source 36 is positioned to direct a beam 37 to optical sensor 38, which, in turn, is connected with counter means 17. The pulsing of the light beam 37 as the teeth 39 intercept light beam 37 is then counted by counter means 17 and converted into increments and then into volume dispensed by computer 22 using the calibrated value stored in its memory.

Figure 3:
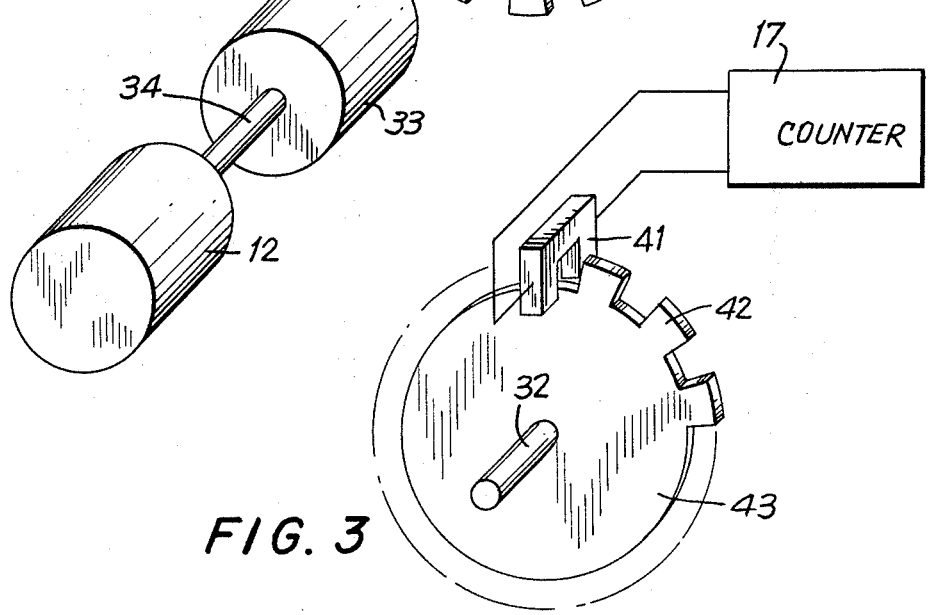

FIG. 3 illustrates counting of the increments by means of an electromagnet 41 positioned for generating electric pulses as iron teeth 42 pass between the poles thereof during rotation of disk 43. Again, the pulses are sent to counter 17.

Figure 4:
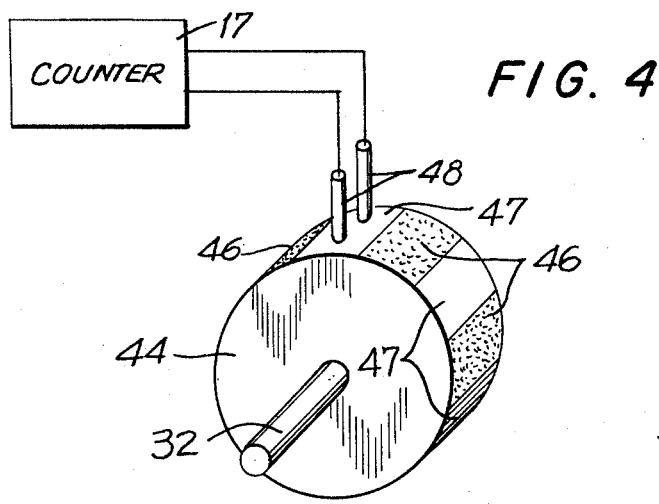

In the device of FIG. 4, the detection means are electrical, cylinder 44 having alternate conductive strips 46 and nonconductive strips 47 thereon. As cylinder 44 rotates, electrical connection between conductive leads 48 is alternatingly made and broken. Counter means 17 notes the number of increments or revolutions or cycles and transmits the data to computer means 22.

Figure 5:
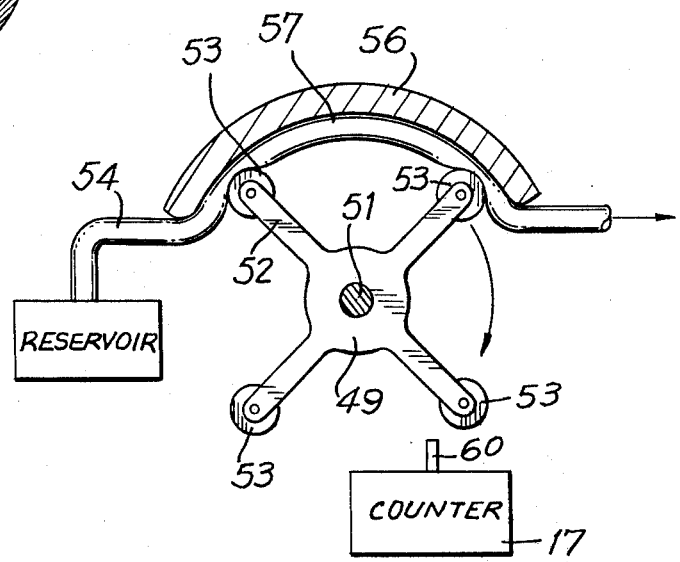
FIG. 5 is a view of counter means for counting increments of fluid mechanically.

In the embodiment of FIG. 5, a frame 49 rotates on shaft 51, shaft 51 being driven by a motor as in FIG. 2. Frame 49 carries a number of equally spaced arms 52, each being fitted at the tip thereof with a roller 53. A tube 54 of a suitable elastomer, such as rubber or a flexible plastic, is disposed against a rigid housing 56 in a position such that each of the rollers 53 compresses the tubing shut as it passes across the tubing. The angle which the housing 56 subtends at the center of shaft 51 is at least slightly greater than the angle between successive arms 52, thereby ensuring that at least one of said rollers will always be in contact with said tubing and closing same at the point of contact therebetween. The increment delivered by the pump will then correspond closely to the volume held in tube section 57 when two of the rollers make contact simultaneously with the tubing and compress same against housing 56. Counter means 17, in this embodiment, is mechanical, the counter means being tripped by contact of roller 53 with finger 60.

The operation of the fluid dispenser can most conveniently be described on the basis of the embodiment shown in FIG. 6. Switch 3 puts the dispenser into manual mode, desirable for priming conduit 58, pump 12 and conduit 14 from reservoir 59. Once these elements are primed, pump switch 1 is activated as described above. The volume to be dispensed in each dose is set into dial 26 by means of thumb wheels, and the number of doses to be dispensed is set into dial 9 by similar thumb wheels. A time-interval thumb wheel switch 8 is provided for setting the time interval between delivery cycles. The dispenser is put into operation by pressing auto switch 4, or, if desired, is operated by a remote foot-control (not shown), in which case, switch 5 is actuated. Alternatively, the remote switch 5 allows for dispensing by an external control signal. Such a signal can be generated by bringing a receiver into receiving position. Hold button 2 makes it possible to interrupt pump operation without loss of data stored in the memory. Reset button 7 provides either an audible or a visual alert signal should the pump stop. Count display 10 is a bi-directional counter that indicates either the total number of doses dispensed or the remaining preset doses to be dispensed, as desired. Clear button 61 resets the display count to zero. Switch 62 is the power on or off switch. In the embodiment shown in FIG. 6, pump means 12 is mounted on the top of the housing 63 holding the computer means 22, counter means 17, motor 13, controller means 23 and calibrator means 27.

As is evident, either tubing 57 or pump means 12 can be replaced in order to change the size of the increment. Furthermore, two or more pump means can be mounted on the same shaft, each pump means having its own conduits and tubing and being connected with its own reservoir for delivery to different receivers simultaneously or delivery of different fluids to a single receiver. Furthermore, only one counter is necessary for counting the increments, the counter and the computer being arranged and constructed for translating or converting revolutions or cycles into increments and thence to volumes for each of the separate pump means.

As aforenoted, one of the most desirable features of the present invention is that the volume of fluid in each increment can readily be redetermined so as to recalibrate the dispenser whenever this is deemed necessary. Activating the calibrator switch 1 removes the previous calibrated value from the memory and inserts the new one. The tubing and other conduits can readily be exchanged or replaced in order to avoid contamination.

Figure 7:
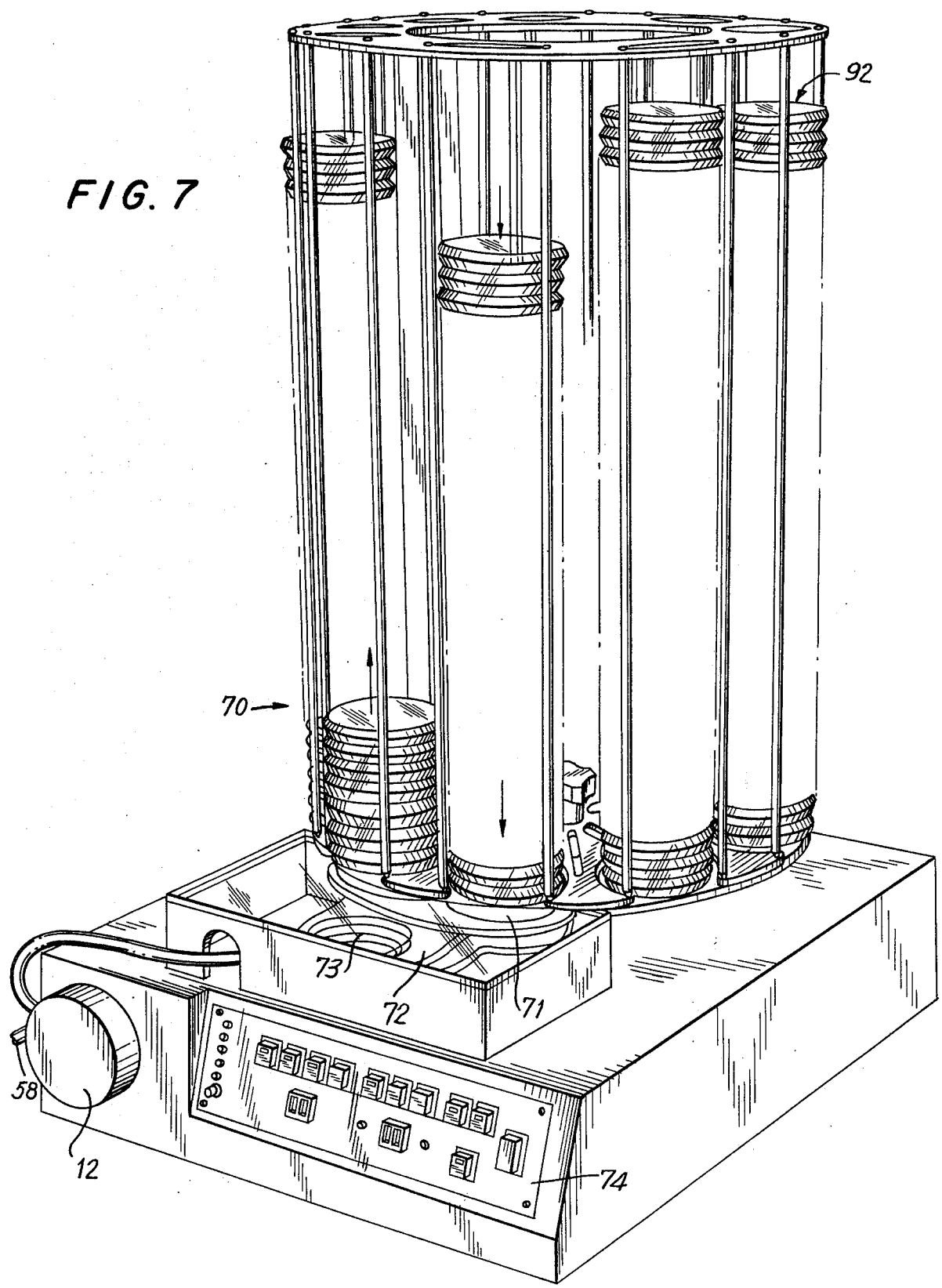
FIG. 7 is another embodiment of the invention including means for charging petri dishes with agar.

The fluid dispenser is particularly useful in controlling the operation of a petri-dish filler. The combination may be constructed in the form of connected but separate units or may be combined into a single unit. Such a single unit is shown in perspective in FIG. 7, wherein stacks of petri dishes 92 are held in a carousel indicated generally by the reference numeral 70. Each stack is successively located over a transport position 71, and the petri dishes are sequentially dropped into an opening in transporter 72, which brings the petri dish to a filling position 73 and separates the cover therefrom. Pump means 12 is then activated to dispense agar through conduit 14 into the petri dish in receiving position 73. In this embodiment, dispensing of each dose is initiated by bringing the uncovered petri dish into receiving position 73. Accordingly, panel 74 is slightly altered from that of FIG. 6 in ways which will be evident to those skilled in the art. Also, panel 74 must provide for rotation of carousel 70 at appropriate intervals and for other operations disclosed in our previous application.

The fluid dispenser disclosed herein is small in size, and low in cost, particularly in view of the precision and accuracy afforded by same. Moreover, it provides great convenience in that calibration and recalibration are easily carried out whether completely automatically or with the cooperation of an operator, and contamination is readily avoided. The pump may be calibrated for a specific tubing, a specific fluid or a specific pump head. Tests have shown that the calibration value can be determined with sufficient precision so that the dispensing volume may be controlled with a precision of ±0.02 ml to ±0.8 ml, depending on the pump head employed.

It will thus be seen that the objects set forth above, among those made apparent from the preceding description, are efficiently attained, and since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A fluid dispenser comprising:
   pump means arranged and constructed for dispensing a fluid dose in increments of essentially equal size;
   calibration collection means for receiving the fluid output of said pump means;
   conduit means connected with said pump means for transfer of said fluid to said calibration collection means;
   counting means for counting the number of increments of fluid pumped by said pump means;
   sensing means for detecting a calibration volume output of said pump means in said calibration collection means;
   computer means having a memory and programmable for dividing on command the number of increments of fluid pumped to said calibration collection means by said calibration volume pumped to said calibration collection means for determining the fluid volume per increment, hereinafter termed "calibrated value," and thereby calibrating said pump;
   manually operable calibration means for causing said "calibrated value" to be stored in said memory;
   means for selecting a volume of fluid to be dispensed to a receiver;
   controller means operatively connected with said pump means and said computer means, said controller means being adapted to cause said computer means to divide the numeric value of said selected volume by said stored "calibrated value", said division determining the necessary number of increments to be dispensed, said controller means being further adapted to cause said pump means to operate and deliver said number of increments, whereby the selected volume of fluid is dispensed to said receiver.

2. The fluid dispenser as defined in claim 1, wherein said conduit means includes a flexible hose positioned for being flexed by said pump means for causing transfer of fluid therethrough.

3. The fluid dispenser as defined in claim 1, wherein said counting means includes optical sensor means for counting the number of increments delivered by said pump means.

4. The fluid dispenser as defined in claim 1, wherein said counting means includes magnetic sensor means for counting the number of increments delivered by said pump means.

5. The fluid dispenser as defined in claim 1, wherein said counting means includes electrical sensor means for counting the number of increments delivered by said pump means.

6. The fluid dispenser as defined in claim 1, wherein said counting means includes mechanical sensor means for counting the number of increments delivered by said pump means.

7. The fluid dispenser as defined in claim 1, wherein said pump means includes a single motor means connected for driving both said pump means and said counting means.

8. The fluid dispenser as defined in claim 1, wherein said controller means is arranged and constructed for operating selectively in one of the following modes:
(a) delivery of a single dose of the selected volume, and
(b) delivery of a selected number of doses of the selected volume.

9. The fluid dispenser as defined in claim 1, wherein said controller means is arranged and constructed for causing said fluid dispenser to deliver selected volumes at selected time intervals.

10. The fluid dispenser as defined in claim 9, wherein said time intervals have a lower limit of zero and setting of said time interval to zero provides for continuous delivery of fluid.

11. The fluid dispenser as defined in claim 1, wherein said fluid dispenser comprises additional pump means, each additional pump means associated with a corresponding conduit means and each additional pump means operatively connected with said computer means, said calibration collection means and said controller means.

12. The fluid dispenser as defined in claim 1, and wherein said fluid dispenser is associated with filling means for automatically charging a plurality of petri dishes with agar.

13. The fluid dispenser as defined in claim 12, wherein said controller means is arranged and constructed for shutting off said fluid dispenser after delivery of said selected volume.

14. The fluid dispenser as defined in claim 12, wherein said controller means is arranged and constructed for shutting off said fluid dispenser after delivery of a selected number of doses of said selected volume.

* * * * *